(12) United States Patent
Beermann

(10) Patent No.: US 6,235,070 B1
(45) Date of Patent: May 22, 2001

(54) RIGID SAND BODY, METHOD FOR PRODUCING THE SAME, USE THEREOF AND METHOD FOR PRODUCING GRAINS OF SAND COATED IN WAX

(76) Inventor: Norbert Beermann, Kaulbachstrasse 61, D-80539 Munich (DE)

( * ) Notice: Subject to any disclaimer, the term of this patent is extended or adjusted under 35 U.S.C. 154(b) by 0 days.

(21) Appl. No.: 09/445,642

(22) PCT Filed: Jun. 12, 1997

(86) PCT No.: PCT/EP97/03082

§ 371 Date: Dec. 9, 1999

§ 102(e) Date: Dec. 9, 1999

(87) PCT Pub. No.: WO98/56520

PCT Pub. Date: Dec. 17, 1999

(51) Int. Cl.[7] ............... B22C 1/00; A61K 7/48; B44C 3/04
(52) U.S. Cl. ............... 51/308; 51/306; 106/271; 106/272; 428/403; 424/420; 264/112; 264/319; 264/328.17
(58) Field of Search ............... 51/308, 306; 106/272, 106/271; 424/417, 420; 428/403, 404; 264/112, 319, 328.17

(56) References Cited

U.S. PATENT DOCUMENTS

| 525,292 | * | 8/1894 | Slicer ............... 106/272 |
|---|---|---|---|
| 3,607,332 | | 9/1971 | Wingfield . |
| 4,537,604 | | 8/1985 | Dawson . |
| 5,108,677 | * | 4/1992 | Ayres ............... 264/112 |
| 5,580,192 | * | 12/1996 | Ogawa et al. ............... 405/263 |
| 5,711,795 | * | 1/1998 | Browning ............... 106/272 |

FOREIGN PATENT DOCUMENTS

| 29 37 843 B1 | 5/1980 | (DE) . |
|---|---|---|
| 34 00 003 A1 | 7/1985 | (DE) . |
| 39 30 413 A1 | 1/1991 | (DE) . |
| 40 39 244 A1 | 6/1992 | (DE) . |
| 196 15 896 A1 | 7/1997 | (DE) . |
| 0 590 186 A1 | 9/1992 | (EP) . |
| 59-169646 | 9/1984 | (JP) . |
| 60-152407 | 8/1985 | (JP) . |
| 4338314 | * 11/1992 | (JP) . |

OTHER PUBLICATIONS

Ullmanns Encyclopadie D. Techn. Chemie, 4. Aufl., BD. 6, 1981, S. 472–477 (No month).

* cited by examiner

Primary Examiner—Michael Marcheschi
(74) Attorney, Agent, or Firm—Mary R. Bonzagni, Esq.; Holland & Bonzagni, P.C.

(57) ABSTRACT

The invention relates to a rigid sand body consisting of a plurality of sand grains adhering to one another and provided with a coating consisting of wax, wherein the sand body is abradable, as well as to a process for its preparation, which is characterized in that sand grains and wax are heated separately from one another at a temperature of 50–90° C., the heated sand grains and the heated, liquid wax are added together and the composition obtained is allowed to cool for solidification. The sand bodies of the invention are particularly suitable as a sand scrub for skin massage or as a modelling or model component. The invention also relates to a process for producing discrete agglomerated sand grains provided with a coating having burls consisting of wax by abrading the sand body of the invention. The resulting abration sand comprising sand grains surrounded by wax are very well suited as sliding and slipping bases.

8 Claims, No Drawings

RIGID SAND BODY, METHOD FOR PRODUCING THE SAME, USE THEREOF AND METHOD FOR PRODUCING GRAINS OF SAND COATED IN WAX

FIELD OF THE INVENTION

The present invention relates to a rigid sand body, a process for its preparation, its use as a sand scrub for skin massage as well as a modelling or model component and a process for production of discrete or agglomerated sand bodies provided with a coating having burls consisting of wax.

BACKGROUND OF THE INVENTION

Hitherto it was conventional to carry out sand fixing with the aid of poisonous and environmentally dangerous materials, such as for example synthetic resin, or with the aid of harmful solvents, such as petroleum, heavy benzine, light benzine and benzene, for example by the $CO_2$ process.

German Offenlegungsschrift 3 930 413 describes a polishing agent necessarily comprising at least 9 components, inter alia, wax and siliceous chalk, but also petroleum, test benzine and special benzine.

German Auslegeschrift 2 937 843 describes the use of compositions comprising a high-molecular binder based on polyvinyl chloride, cellulose ether or ceresin wax, plasticisers and/or solvents as well as conventional additives as a kneading and modelling composition, wherein the composition contains aluminium hydroxide as filler. It was thus the particular aim to provide a kneading and modelling composition which has high colour intensity and colour fidelity.

European application 0 590 186 describes a core for fine-casting of carbon steels by the lost-wax process and before firing the core (green core), which is characterised by the following constituents: quartz having grains of round or polyhedral form as residual component, zirconium and aluminium oxide approximately in the same weight percentage as zirconium, but lower than quartz, wax as binder and in the same weight percentage stearin. Stearin and wax are thus used as binder approximately in the same weight percentages, wherein the different properties of stearin and wax are emphasised in particular.

SUMMARY OF THE INVENTION

The aim of the invention is to provide a rigid sand body which can be obtained in any shape and size, and which does not contain toxic and environmentally dangerous materials. Furthermore, a simple and cost-effective process for its preparation should be provided, in which likewise toxic and environmentally dangerous materials are not required.

The object of the invention is thus a rigid sand body consisting of a plurality of sand grains adhering to one another and provided with a coating consisting of wax, wherein the sand body is abradable.

DETAILED DESCRIPTION OF THE INVENTION

According to the invention, it has been shown surprisingly that a sand body consisting only of sand and wax, the wax surrounding the individual sand grains as a coating, may be made available in any shape and size, and has a property profile which permits diverse possibilities for use of the sand body. The sand body is fixed by coating of the sand grains consisting of wax. The surface of the sand body may be changed easily by abrading or cutting tools, sand abrasion being achieved by sand grains surrounded by wax.

The sand which can be used in the invention is not subject to any particular limitation. The sand grains conventionally have a diameter of 0.06 to 2 mm and are designated according to grain size as fine sand (equivalent diameter of conventionally 0.06–0.2 mm), average sand (equivalent diameter of conventionally 0.2–0.63 mm) or coarse sand (equivalent diameter of conventionally 0.63–2.0 mm). Dune-sand of sea beaches may be used by way of example, the grains of which conventionally have a diameter of about 1 mm or less.

The wax used in the invention is also not subject to any particular limitation. Wax is normally kneadable at room temperature, melting without decomposition above 40° C., has relatively low viscosity above the melting temperature range and is not stringy. Waxes usually transfer to the molten, low-viscosity state approximately between 50 and 90° C. Natural, chemically modified and synthetic waxes are suitable for the purposes of the invention.

Examples of natural waxes are vegetable waxes, such as candelilla wax, carnauba wax, Japan tallow wax, esparto grass wax, cork wax, guaruma wax, rice germ oil wax, sugarcane wax, ouricury wax and montan wax, animal waxes, such as beeswax, shellac wax, spermaceti wax and lanolin, mineral waxes, such as ceresin and ozokerite or earth wax, petrochemical waxes, such as petrolatum, paraffin waxes and microwaxes.

Examples of chemically modified waxes are hard waxes, such as montan ester waxes, sasol waxes and hydrogenated jojoba waxes.

Examples of synthetic waxes are polyalkylene waxes and polyethylene glycol waxes.

Natural waxes, such as beeswax, are particularly preferred for certain applications of the sand bodies of the invention. If required, the waxes may also be coloured or treated with fragrances.

The object of the invention is also a process for preparing the above-mentioned sand body, which is characterised in that sand grains and wax are heated separately from one another at a temperature of 50–90° C., preferably 60–90° C., the heated sand grains and the heated, liquid wax are added together and the composition obtained is allowed to cool for solidification.

The process of the invention thus facilitates fixing of the sand merely by supplying energy without using synthetic resins and any kind of solvent. The volume ratio of sand to wax may thus suitably be about 4:1, corresponding to a weight ratio of about 8:1, it being possible to increase this ratio even to about 16:1, for example with the aid of compressed air pumps.

According to a preferred embodiment, the adding together is carried out such that the heated, liquid wax is cast onto a layer of heated sand grains. The liquid wax thus seeps in the hot sand like water. At normal sand temperatures of 20 to 30° C. on the other hand, the liquid wax would not be able to penetrate. After trickling of the liquid wax, large and small sand bodies may then be formed in the phase of cooling using technical auxiliaries. This is effected in suitable manner in that the composition obtained is pressed into a mould before cooling. Alternatively, preparation of the sand bodies of the invention may also be effected such that heated sand is placed in a required mould or the sand is heated in the mould and the heated, liquid wax is cast onto the heated sand grains. After cooling, these sand bodies are fixed and show slight sand abrasion on the surface on contact, that is they are abradable. As a result of this abradability the cooled, rigid sand body may now be processed easily using technical auxiliaries. Likewise, the shape of the sand body may be changed easily by abrading tools.

As a result of renewed softening by means of supplying heat to individual surfaces of the sand body already cooled, other sand bodies may be attached to these heated surfaces, assuming that the surface to be attached has been softened and heated for the second sand body as well.

The process of the invention is particularly advantageous from ecological points of view and from the point of view of cost-saving, since sand fixing may be carried out by means of solar energy alone depending on the geographical location.

Fine-grain sand, such as exists for example as dune-sand on sea coasts, is suitable for the purposes of the invention, as mentioned above. The latter conventionally has a diameter of about 1 mm or less and shimmers in all colours in the dry state under the microscope. By way of example for a light dune-sand from the Camargue, the white colours and transparent crystal grains predominate. Occasionally it is also possible to see brown and black sand grains. Almost all shapes of the grains are rounded, but they are not spheres but small cuboids or polyhedrons. However, many elongated bodies can also be seen.

The sand grains surrounded by wax of the fixed sand body of the invention likewise shimmer in all colours under the microscope, but now shine much more strongly, Even brown and dark sand grains show a shimmering gloss after coating, in contrast to pure sand. This strong gloss comes from the wax coating of the individual sand grains. Furthermore, it is possible to determine under the microscope that long white or even transparent long burls of wax are situated on quite a few sand grains. They project in some cases into the hollow cavities and form the bridges between the sand grains. However, most sand grains are pressed so closely against one another that these burls can no longer be seen.

Since the fixed sand bodies are abradable, after scratching the fixed sand body a further surface image is produced. Under the microscope the surrounded sand grains are now in turn seen to shimmer in all colours, but the large occasional burls have disappeared. Instead very many small burls can be seen on each sand grain. Without being bound to a theory it is assumed that the individual sand grains of the sand body of the invention are joined to one another via innumerable wax bridges or burls, and the sand body thus achieves considerable overall strength.

The object of the invention is also a process for producing discrete or agglomerated sand grains provided with a coating having burls consisting of wax by abrading the sand body of the invention.

As a result of such abrasion of the sand body, a new abrasion or crumb sand comprising sand grains surrounded by wax is produced. In most cases 5–10 coated sand grains thus stay together and continue to be adhered to one another in spite of the abrasion of the sand body. It can be seen under the microscope that bridges or burls go in all directions from these coated sand grains. They may be joined easily again with other coated sand grains via these burls. This occurs by simply pressing together the coated sand grains, even in the cooled state. A self-adhering sand is thus provided according to the invention in a manner not known hitherto.

Coated sand grains pressed together in this way now show a different surface image under the microscope. It is possible to see the sand grains only faintly, hollow cavities between them can no longer be determined, large burls on the grains can likewise no longer be seen, but the transparent wax coating is seen predominately. The overall surface is adhered firmly using a wafer-thin wax coating, that is all sand grains are joined firmly to one another on the surface. Hence, one sand grain may no longer break away from the surface and the abradability is lost or severely restricted.

The rigid sand bodies of the invention open up diverse possibilities for use. According to one aspect of the invention, the sand bodies of the invention are used as a sand scrub for skin massage. The sand scrub slides over the skin without injuring it due to the grainy structure of the fixed sand body and its abradability as well as the pad-like wax coating of each individual sand grain. Dead skin particles are thus entrained and the skin is freed of undesirable skin flakes. Some of the latter remain adhered to the sand scrub or to the abrasion sand which remains lying on the skin. Since the sand grains surrounded by wax also have excellent slidability in addition to the adhesive property, all sand residues may be removed with a dry towel by wiping after the body massage. A further effect of the skin massage using the sand scrub consists in that the young skin is not only freed of skin flakes but is also supplied with blood at the same time. The longer the massage lasts, the more the sand scrub adheres, partly due to the skin flakes, partly due to the heat produced by friction. It is therefore advisable to renew the sand scrub from time to time on the surface, for example by scratching by means of a knife. The sand scrub is then completely reusable.

A further advantage with respect to current skin massaging processes lies in the fact that no creams, lotions or gels have to be used, but the skin remains completely dry, which is very desirable for sensitive skin. Subsequent cleaning with water is likewise not necessary. Beeswax is preferably used as the wax for the sand scrub, so that the sand scrub consists only of natural materials.

According to a further aspect of the invention, the sand body of the invention is used as a modelling or model component. Any figures or model structures, such as statues, sculptures, vases, plates, keys or prostheses, which have similar hardness to sandstone bodies but can be processed much more easily, may thus be produced by easy processing of the sand bodies using very little expense in terms of time, energy and cost. It is particularly advantageous that all waste occurring during processing may thus be melted again easily, and specifically even using solar energy, likewise all figures no longer used. They are thus available as starting material for new figures and new products, such as for material use when laying garden ponds, coating tennis courts, bobsleigh runs or for coating skating rinks.

As already mentioned above, discrete or agglomerated sand grains provided with a coating having burls consisting of wax may be produced by abrading the sand body of the invention. These coated sand grains are very well suited as sliding and slipping bases, as fillers of cracks or holes, or as padding material in long-jump pits. Since these prepared sand grains are water-repellant due to the wax coating, they are also suitable for covering materials in the open.

The invention is illustrated in more detail using the following exemplary embodiments,

EXAMPLE 1

The Sand Scrub as Skin Massaging Device

The fixed sand bodies are pressed into soap-size casting moulds while still in the heated phase and thus wrapped in aluminium foil. After cooling, the aluminium foil is removed and the sand scrub is rubbed to be ready-for-use on the surface using a knife, that is it is roughened.

EXAMPLE 2
Production of a Sculpture or a Model Component

The fixed sand bodies are pressed into a casting mould lined with aluminium foil while still in the heated phase, the dimensions of the casting mould being greater than those of the model component to be produced or the sculpture to be produced. After cooling, the solidified sand body is tapped out of the casting mould and the aluminium foil is removed or scraped off. The sand body may then be processed easily using tools.

In mass production of model components, a casting mould is used which, as regards shape and dimensions, already corresponds approximately to the model component to be produced or the sculpture to be produced. Use of an aluminium foil is thus not absolutely necessary. The outer walls of the casting mould may be heated gently to facilitate release of the sand body from the casting mould. It is thus possible to remove the pre-moulded sand body easily from the mould without having to tap it.

EXAMPLE 3
Production of Coated Abrasion Sand

The fixed sand bodies are pressed into casting moulds lined with aluminium foil while still in the heated phase, the dimensions of the casting moulds being similar to flower boxes. After cooling, the solidified sand body blocks are tapped out of the casting mould and stacked.

The solidified sand body blocks, which are abradable, are processed using tools or machines so that abrasion sand surrounded by wax is rubbed away continuously until complete resolution of the individual sand body blocks. Any residue of the blocks remaining may be re-used for renewed production of sand bodies.

The coated abrasion sand thus obtained may be stored in warehouses until it is transported away to the required places of use, such as covered, artificial snowboard runs, ski runs and cross-country ski runs or to building sites for repair work.

We claim:

1. A rigid and abradable sand body consisting essentially of a plurality of sand grains having a wax coating thereon, wherein said wax coating has bridges or burls, and wherein said wax coated sand grains adhere to one another.

2. The rigid and abradable sand body of claim 1, wherein said sand grains have a diameter of from 0.06 to 2 millimeters.

3. The rigid and abradable sand body of claim 1, wherein said sand grains have a diameter of less than or equal to 1 millimeter.

4. A process for preparing a rigid and abradable sand body comprising:

heating a plurality of sand grains to a temperature of from 50 to 90° C.;

separately heating wax to a temperature of from 50 to 90° C. to liquify said wax;

combining said heated sand grains and said liquified wax by casting said liquified wax on a layer of said heated sand grains to form a composition having a wax coating thereon; and allowing said composition to cool and solidify to form a rigid and abradable sand body, wherein the wax coating has bridges or burls.

5. The process of claim 4, which further comprises pressing said composition into a mold prior to allowing said composition to cool and solidify.

6. A process for preparing discrete or agglomerated sand grains with a wax coating thereon having burls, wherein said process comprises: abrading a rigid sand body comprising a plurality of sand grains having a wax coating thereon, wherein said wax coated sand grains adhere to one another.

7. A method of massaging skin, wherein said method comprises: contacting said skin with a rigid and abradable sand body which consists essentially of a plurality of sand grains having a wax coating thereon, wherein said wax coating has bridges or burls, and wherein said wax coated sand grains adhere to one another.

8. A method for producing figures or model structures, wherein said method comprises: combining a plurality of heated sand grains and liquified wax by casting said liquified wax on a layer of said heated sand grains to form a composition having a wax coating thereon; pressing said composition into a mold having dimensions that correspond to those of said figure or model structure to be produced; allowing said composition to cool and solidify; and removing said cooled and solidified figure or model structure from said mold, wherein the wax coating has bridges or burts.

* * * * *